United States Patent [19]

Shelley et al.

[11] Patent Number: 5,505,961
[45] Date of Patent: Apr. 9, 1996

[54] GELATIN CAPSULES CONTAINING A HIGHLY CONCENTRATED ACETAMINOPHEN SOLUTION

[75] Inventors: Rickey S. Shelley, Largo; Youching Wei, Clearwater; Deborah Linkin, Madeira Beach, all of Fla.

[73] Assignee: R. P. Scherer Corporation, Troy, Mich.

[21] Appl. No.: 263,630

[22] Filed: Jun. 22, 1994

Related U.S. Application Data

[63] Continuation-in-part of Ser. No. 102,464, Aug. 5, 1993, abandoned.

[51] Int. Cl.⁶ .................................................. A61K 9/48
[52] U.S. Cl. ........................ 424/451; 424/455; 424/456; 424/457
[58] Field of Search .............................. 424/457, 456, 424/455, 451

[56] References Cited

U.S. PATENT DOCUMENTS 3,956,490  5/1976  Higuchi .................................... 424/233
5,071,643  12/1991  Yu ............................................. 514/570

FOREIGN PATENT DOCUMENTS

0243930A1  11/1987  European Pat. Off. .

*Primary Examiner*—D. Gabrielle Phelan
*Attorney, Agent, or Firm*—Banner & Allegretti

[57] ABSTRACT

A method is disclosed for increasing the solubility of acetaminophen alone or in combination with antihistamines, antitussives, decongestants, and expectorants to form a clear solution for encapsulation into a softgel. The acetaminophen is solubilized alone or in combination with the above ingredients by mixing with polyethylene glycol, propylene glycol, water, polyvinylpyrrolidone and potassium (or sodium) acetate. This invention increases the solubility of the acetaminophen to obtain the same size softgel for a 325 mg dose as is presently available for a 250 mg dose softgel product. The disclosed solvent system is useful because it provides for a highly concentrated solution of acetaminophen capable of encapsulation in a small enough capsule to permit easy swallowing.

16 Claims, No Drawings

GELATIN CAPSULES CONTAINING A HIGHLY CONCENTRATED ACETAMINOPHEN SOLUTION

This application is a continuation-in-part of U.S. patent application Ser. No. 08/102,464, filed Aug. 5, 1993, now abandoned.

BACKGROUND OF THE INVENTION

1. Field of the Invention

The present invention relates to soft and hard shell gelatin capsules encapsulating a pharmaceutically acceptable fill containing acetaminophen.

Soft gelatin capsules or softgels are predominantly used to contain liquids wherein the active ingredients are present in the dissolved or suspended state. Filled one-piece softgels have been widely known and used for many years and for a variety of purposes. Because softgels have properties that are quite different from telescoping two-piece, hard shell capsules, the softgels are capable of retaining a liquid fill material. The fill material may vary from industrial adhesives to bath oils. More commonly, however, the softgels are used to enclose consumable materials such as vitamins and pharmaceuticals in a liquid vehicle or carrier.

A particularly good bioavailability of the pharmacologically active substance is attained if the active substance is successfully dissolved in a suitable solvent and the encapsulated solution is administered to the patient. The term "active substance" as used herein describes any active substance that can be orally administered in capsule form. This term includes pharmaceuticals, dietary supplements, vitamins and the like.

Solutions also provide the best liquid form to obtain optimal "content uniformity" in softgel fill. In addition, a solution provides a faster and more uniform absorption of a pharmaceutical agent than a suspension. Because of these distinct technical advantages, solutions are preferred over suspensions or other dispersions.

Producing a highly concentrated solution of any acidic, amphoteric or basic pharmaceutical agent is useful because it permits the encapsulation of a unit dose of the pharmaceutical agent in a softgel capsule that is small enough to permit easy swallowing. Filling a unit dose in a small softgel capsule to permit easy swallowing is useful because it increases patient acceptance of the medication. Patient acceptance is especially important in the case of medications, because patient acceptance of the medication is a substantial step towards solving one of the major problems of drug therapy—patient noncompliance with the prescribed regimen.

A further utility of highly concentrated solutions is enhancement of bioavailability of the dissolved pharmaceutical agent. Enhanced bioavailability occurs as a result of delivering the pharmaceutical agent already in solution at the site of absorption, permitting a faster and more uniform absorption to occur.

However, a problem in the art is that an appropriate solution of the pharmaceutical agent cannot always be achieved. One constraint is size. Often, it is not possible to dissolve the pharmaceutical agent in a volume of solvent small enough to produce a softgel that is appropriate from the standpoint of economics and patient acceptance. Another constraint, is the solvent itself. The solvent must have sufficient solvating power to dissolve a large amount of the pharmaceutical agent to produce a highly concentrated solution, and yet not hydrolyze, dissolve, or tan the softgel capsule shell.

In many cases, this problem would have been solved by using the enhanced solubility system described in U.S. Pat. No. 5,071,643. U.S. Pat. No. 5,071,643 (Yu et al.) discloses, inter alia, soft gelatin capsules containing highly concentrated acetaminophen solutions comprising 25–40% by weight acetaminophen, 0.4–1.0 moles of hydroxide ion per mole of acetaminophen (provided, for example, by potassium hydroxide), and 1–20% by weight water in a polyethylene glycol base, such as PEG 600. A specific example of a 35% concentrated solution of acetaminophen is shown in Example VI of this patent. However, it has been recently determined that the sodium hydroxide or potassium hydroxide required to solubilize the acetaminophen at very high concentrations increased the pH of the polyethylene glycol solution to greater than 12. This resulted in the degradation of the acetaminophen and the dissolving of the softgel shell.

Thus, the problem of finding an appropriate solvent system for a soft gelatin capsule fill still exists for acetaminophen. It has been difficult to achieve a soft gelatin capsule of small enough size to be acceptable to patients, i.e., small enough to swallow, while still including in that capsule a sufficient amount of acetaminophen in solution to provide an effective unit dose. Thus, there is a need in the art for a soft gelatin capsule containing a fill in which acetaminophen is dissolved in a solvent system in a high enough concentration to provide an effective unit dose in a patient acceptable size capsule while at the same time avoiding degradation of the acetaminophen and the capsule shell.

SUMMARY OF THE INVENTION

It is a primary object of the present invention to provide a solvent system that is capable of producing highly concentrated solutions of acetaminophen that are suitable for filling into softgels.

The solvent system of the present invention is useful in that it provides for the encapsulation of a pharmaceutical agent, acetaminophen, in a volume of solution that is small enough to permit easy swallowing. It further provides for the preparation of highly concentrated solutions of the pharmaceutical agent to obtain the same size softgel capsule for a higher dosage as is presently commercially available for a lower dose softgel product.

The present invention also relates generally to a pharmaceutical carrier system or "solvent system" for enhancing the solubility of acetaminophen alone or in combination with other pharmaceutical agents, such as antihistamines, antitussives, decongestants, and expectorants, to form a clear solution for encapsulation into a softgel. The inventive solution comprises in its simplest form a mixture of about 20%–40% by weight acetaminophen, about 18%–65% by weight polyethylene glycol, about 0%–15% by weight propylene glycol, about 0%–15% by weight water, about 0–15% by weight polyvinylpyrrolidone, and about 0.6%–25% by weight alkali metal acetate, such as potassium or sodium acetate. In additional embodiments of the present invention, the inventive solutions comprise a mixture of about 20%–40% by weight acetaminophen, about 18% or 30% to 52% or 65% by weight polyethylene glycol, about 0% to 12% or 15% propylene glycol, about 0% to 12% or 15% water, about 0% to 12% of 15% polyvinylpyrrolidone, and about 0.6% or 1% to 20% or 25% by weight alkali metal acetate.

In addition, the present invention increases the solubility of the acetaminophen to obtain the same size softgel for a 325 mg dose as is presently available for a 250 mg dose softgel product. This is believed to be achieved by using a solubilizing agent such as potassium or sodium acetate to increase the pH of the polyethylene glycol solution, which in turn increases the solubility of the weak acid acetaminophen.

Without using the solubility system of the present invention, the maximum amount of acetaminophen that could be dissolved in a polyethylene glycol, propylene glycol, water, and polyvinylpyrrolidone mixture was 27% by weight. In the present invention, an alkali metal acetate is used in the solvent system in the absence of the strong base taught in Yu et al. By the addition of the potassium acetate or sodium acetate, the solubility of acetaminophen could be increased to 32% or greater to achieve the same size softgel for a larger dose of acetaminophen without substantial degradation of the drug or the capsule shell caused by a strong base.

Presently, acetaminophen is commercially solubilized by addition to a mixture of polyethylene glycol, propylene glycol, water and polyvinylpyrrolidone. But, as stated previously, this method will allow only 27% of the acetaminophen to be solubilized. The solubility system of the Yu et al. disclosure was tried but was unsatisfactory because of the resultant high pH of the solution. The addition of the potassium (sodium) acetate, as set forth in the present invention, allows the acetaminophen solubility to be increased to 32% or greater.

It is a specific object of the present invention to provide a soft gelatin capsule for subsequent oral administration encapsulating a fill. The fill comprises a pharmaceutically acceptably highly concentrated solution of acetaminophen, i.e., the acetaminophen dissolved in a solvent system. The inventive solution comprises a mixture of from about 20%–40% by weight acetaminophen, from about 18 to about 65% polyethylene glycol, from about 0 to about 15% propylene glycol, from about 0 to about 15% water, from about 0 to about 15% by weight polyvinylpyrrolidone, and from about 0.6% to about 25% of an alkali metal acetate, all by weight of the total solution. In additional embodiments of the present invention, the inventive fill comprises a solution of about 20%–40% by weight acetaminophen, about 18% or 30% to 52% or 65% by weight polyethylene glycol, about 0% to 12% or 15% propylene glycol, about 0% to 12% or 15% water, about 0% to 12% of 15% polyvinylpyrrolidone, and about 0.6% or 1% to 20% or 25% by weight alkali metal acetate. The alkali metal acetate is present in an amount sufficient to increase the maximum solubility of the acetaminophen in the solution.

The preferred alkali metal acetates are sodium acetate and potassium acetate. In preferred embodiments, the polyethylene glycol that forms a portion of the solvent system has an average molecular weight ranging between about 200 and about 800. In preferred embodiments, the alkali metal acetate is present in amounts from about 3% to about 20% of the solution. Other objects and embodiments of the present invention will be described in the following description of the preferred embodiments and the claims.

DETAILED DESCRIPTION OF THE PREFERRED EMBODIMENT

The invention encompasses highly concentrated solutions of acetaminophen wherein the prepared solutions are particularly suitable for softgel filling. In addition to the acetaminophen, other known active agents are suitable for use with the solvent system of this invention and may be either acidic, basic, amphoteric or neutral compounds.

This invention may be used to manufacture softgels containing 325 mg acetaminophen alone or in combination with the other types of ingredients described above as a clear solution. These softgels would then be of the approximate size of the present 250 mg acetaminophen product.

The soft gelatin capsules that are useful with the present invention include conventional soft gelatin shells. Capsules useful in the present invention may be made by the conventional rotary die process.

In its most basic form, the inventive fill for soft gelatin capsules include acetaminophen, polyethylene glycol and an alkali metal acetate. Using the present invention, concentrations of acetaminophen in the resulting solution may be upwards of about 40% by weight of the solution. However, the present invention also contemplates encapsulation of lower concentrations of acetaminophen ranging down to about 20% by weight of the solution. The use of pharmaceutical grade acetaminophen USP is preferred.

Various polyethylene glycols may be used in the present invention having average molecular weights between about 200 and about 800, most preferably between about 400 and about 600. A single molecular weight polyethylene glycol may be used or mixtures of various molecular weight polyethylene glycols may be used. In the case of mixtures, small proportions of polyethylene glycols outside of the preferred average molecular weight ranges cited above may be used in admixture with polyethylene glycols within the preferred ranges. The molecular weights of the polyethylene glycols used in the present invention should be selected such that the resulting solution has viscosity compatible with the filling equipment contemplated for production of the soft gelatin capsules. The solvent system typically will contain from about 18% to about 65% polyethylene glycol by weight of the solution, most preferably from about 30% to about 52% or 60%.

By altering the polyethylene glycol used, the present invention may be easily adapted for use with hard shell gelatin capsules. By raising the average molecular weight of the polyethylene glycol used, a semi-solid or solid solution of acetaminophen may be prepared that can suitably filled into conventional hard shell gelatin capsules according to known methods. In such cases, polyethylene glycols having an average molecular weight from about 600 to about 10,000, preferably from 2,000 to about 8,000, can be used to prepare a hard shell gelatin capsule fill solution that is semi-solid. Suitable fills for use in hard shell gelatin capsules would preferably have viscosities of about 20,000 to about 40,000 centipoise and up at 38° C.

Polyethylene glycols having an average molecular weight between about 10,000 to about 100,000, preferably about 15,000 to about 60,000, can be used to produce a hard shell gelatin fill solution that is solid. The polyethylene glycol in these instances would be used in the same amounts with respect to the total weight of the solution as in the case of soft gelatin capsule fills. Also, mixtures of various polyethylene glycols can be used to achieve suitable semi-solid and solid fill solutions.

The inventive fills also include at least one alkali metal acetate, though mixtures of alkali metal acetates are contemplated to fall within the scope of the present invention. The two most preferred alkali metal acetates are sodium acetate and potassium acetate. These two are preferred because of their general availability and cost relative to the other alkali metal acetates. It is contemplated, however, that the alkali metal acetates known to the art may be used, such as sodium acetate trihydrate.

The alkali metal acetate(s) selected is used in an amount from about 0.6% to about 25% by weight of the solution, more preferably between about 1% or 3% and 20% or 25%. The alkali metal acetate selected is also present in an amount sufficient to increase the maximum solubility of the acetaminophen in the solution. In other words, the acetate should be present in an amount that results in an acetaminophen solution having a greater concentration of acetaminophen than the concentration of acetaminophen in the identical solution without the acetate. This is referred to as an enhanced solubility amount of alkali metal acetate.

The person of ordinary skill in the art can, through easy and routine experimentation, determine the amount of the selected acetate that will result in the acetaminophen fill solution of maximum concentration. For this purpose, a series of solutions of a particular solvent base with varying amounts of the acetate may be prepared. To each solution, acetaminophen is added until no more dissolves and the concentration of acetaminophen in each resulting saturated solution is then determined. These data points will establish a curve of acetaminophen concentration versus acetate concentration that will allow a person of ordinary skill in the art to determine the best particular level of acetate to be used with a particular solvent base.

Three optional adjuvants may be added to the inventive fill solution: propylene glycol, water and/or polyvinylpyrrolidone. Propylene glycol may be present in amounts from about 0% to about 15% by weight of the solution, more preferably from about 3% to about 10% or 12%. Water may be present in amounts ranging from about 0% to about 15% by weight of the solution, more preferably from about 3% to about 10% or 12%. Finally, polyvinylpyrrolidone may be present in amounts from about 0% to about 15% by weight of the solution, more preferably between 3% and 10% or 12%. Polyvinylpyrrolidone useful in the present invention may have average molecular weights ranging between about 15,000 and 120,000, more preferably between about 24,000 and 32,000.

Because a strong base need not be used to enhance the solubility of the acetaminophen in the present invention, the acetaminophen in the inventive solution is typically not present in its salt form. Thus, the acetaminophen that is dissolved in high concentrations in the inventive solution can conform to the U.S.P monograph for acetaminophen as confirmed by nmr analysis.

The following examples are given by way of illustration only and in no way should be construed as limiting the invention in spirit or in scope, as many modifications in materials and method will be apparent to those skilled in the art.

EXAMPLE 1

A mixture of polyethylene glycol (about 18% to about 65% by weight), propylene glycol (about 0% to about 15% by weight), and water (from about 0% to about 15% by weight) is prepared and mixed until homogenous. Polyvinylpyrrolidone (or Povidone) (from about 0% to about 15% by weight) is added to the above mixture slowly while stirring. This mixture is stirred until dissolved. Acetaminophen (from about 20% to about 40% by weight) is added slowly, along with other optional ingredients, while stirring. This mixture is stirred until homogenous. Potassium and/or sodium acetate (from about 0.6% to about 25% by weight) is added. While mixing, the mixture is heated and a temperature between 120° to 150° F. is maintained. The mixture is stirred until dissolved and a clear solution is formed. The mixture is cooled and deaerated. The mixture is then encapsulated in conventional soft gelatin capsules using a conventional rotary die process. The dry finished softgels are dried to an appropriate hardness and fill moisture.

EXAMPLE 2

The following formulations A through H were prepared according to the present invention in accordance with the procedures of Example 1.

|  | % |
|---|---|
| A. | |
| PEG 400 | 38.5 |
| Propylene Glycol | 5.0 |
| Povidone | 5.0 |
| Acetaminophen | 32.0 |
| Sodium Acetate Trihydrate Solution | 19.5 |
| TOTAL | 100.0 |
| B. | |
| PEG 400 | 39.4 |
| Propylene Glycol | 5.0 |
| Povidone | 5.0 |
| Acetaminophen | 32.0 |
| Potassium Acetate | 10.6 |
| Water | 8.0 |
| TOTAL | 100.0 |
| C. | |
| PEG 600 | 39.39 |
| Propylene Glycol | 5.0 |
| Povidone | 7.0 |
| Dextromethorphan HBr | 1.47 |
| Pseudophedrine HCl | 2.94 |
| Doxylamine Succinate | 0.61 |
| Acetaminophen | 31.86 |
| Potassium Acetate | 3.73 |
| Water | 8.0 |
| TOTAL | 100.0 |
| D. | |
| PEG 400 | 41.5 |
| Propylene Glycol | 3.0 |
| Povidone | 2.35 |
| Dextromethorphan HBr | 1.47 |
| Pseudophedrine HCl | 2.94 |
| Doxylomine Succinate | 0.61 |
| Acetaminophen | 31.86 |
| Potassium Acetate | 8.27 |
| Water | 8.00 |
| TOTAL | 100.0 |
| E. | |
| PEG 400 | 43.91 |
| Povidone | 5.0 |
| Dextromethorphan HBr | 1.47 |
| Pseudophedrine HCl | 2.94 |
| Doxylamine Succinate | 0.61 |
| Acetaminophen | 31.86 |
| Potassium Acetate | 6.21 |
| Water | 8.0 |
| TOTAL | 100.0 |
| F. | |
| PEG 400 | 39.92 |
| Propylene Glycol | 3.00 |
| Povidone | 5.00 |
| Acetaminophen | 35.00 |
| Potassium Acetate | 9.08 |
| Water | 8.00 |
| TOTAL | 100.0 |

-continued

| | % |
|---|---|
| G. | |
| PEG 400 | 34.48 |
| Propylene Glycol | 2.58 |
| Povidone | 4.30 |
| Acetaminophen | 37.42 |
| Potassium Acetate | 12.14 |
| Water | 9.08 |
| TOTAL | 100.0 |
| H. | |
| PEG 400 | 33.42 |
| Propylene Glycol | 3.0 |
| Acetaminophen | 40.0 |
| Potassium Acetate | 15.58 |
| Water | 8.0 |
| TOTAL | 100.0 |

*Dissolve 15 gm Sodium Acetate Trihydrate in 5 g water with heat

What we claim is:

1. A soft gelatin capsule for subsequent oral administration having a soft gelatin shell encapsulating a fill, the fill consisting essentially of a pharmaceutically acceptable highly concentrated solution of acetaminophen comprising from about 20% to about 40% by weight acetaminophen, from about 18% to about 65% polyethylene glycol by weight, said polyethylene glycol having an average molecular weight of between about 200 and about 800, from about 0% to about 15% propylene glycol by weight, from about 0% to about 15% water by weight, from about 0% to about 15% polyvinylpyrrolidone by weight and from about 0.6% to about 25% of an alkali metal acetate by weight, the alkali metal acetate being present in an amount sufficient to increase the maximum solubility of the acetaminophen in the solution, the alkali metal acetate being selected from the group consisting of sodium acetate and potassium acetate.

2. The capsule according to claim 1 wherein the polyethylene glycol has an average molecular weight of between about 400 and about 600.

3. The capsule according to claim 1 wherein said alkali metal acetate is present in an amount from about 3% to about 20% by weight.

4. The capsule according to claim 1 wherein the fill additionally comprises a second pharmaceutical agent in addition to acetaminophen, the second pharmaceutical agent being selected from the group consisting of antihistamines, antitussives, decongestants and expectorants.

5. A soft gelatin capsule for subsequent oral administration having a soft gelatin shell encapsulating a fill, the fill consisting essentially of a pharmaceutically acceptable highly concentrated solution of acetaminophen comprising from about 20% to about 40% by weight acetaminophen, from about 30% to about 65% polyethylene glycol by weight, said polyethylene glycol having an average molecular weight of between about 200 and about 800, from about 0% to about 15% propylene glycol by weight, from about 0% to about 15% water by weight, from about 0% to about 15% polyvinylpyrrolidone by weight and from about 1% to about 25% of an alkali metal acetate by weight, the alkali metal acetate being present in an amount sufficient to increase the maximum solubility of the acetaminophen in the solution, the alkali metal acetate being selected from the group consisting of sodium acetate and potassium acetate.

6. The capsule according to claim 5 wherein the polyethylene glycol has an average molecular weight of between about 400 and about 600.

7. The capsule according to claim 5 wherein said alkali metal acetate is present in an amount from about 3% to about 20% by weight.

8. The capsule according to claim 5 wherein the fill additionally comprises a second pharmaceutical agent in addition to acetaminophen, the second pharmaceutical agent being selected from the group consisting of antihistamines, antitussives, decongestants, and expectorants.

9. A soft gelatin capsule for subsequent oral administration having a soft gelatin shell encapsulating a fill, the fill consisting essentially of a pharmaceutically acceptable highly concentrated solution of acetaminophen comprising from about 20% to about 40% by weight acetaminophen, from about 18% to about 52% polyethylene glycol by weight, said polyethylene glycol having an average molecular weight of between about 200 and about 800, from about 0% to about 12% propylene glycol by weight, from about 0% to about 12% water by weight, from about 0% to about 12% polyvinylpyrrolidone by weight and from about 0.6% to about 20% of an alkali metal acetate by weight, the alkali metal acetate being present in an amount sufficient to increase the maximum solubility of the acetaminophen in the solution, the alkali metal acetate being selected from the group consisting of sodium acetate and potassium acetate.

10. The capsule according to claim 9 wherein the polyethylene glycol has an average molecular weight of between about 400 and about 600.

11. The capsule according to claim 9 wherein said alkali metal acetate is present in an amount from about 3% to about 20% by weight.

12. The capsule according to claim 9 wherein the fill additionally comprises a second pharmaceutical agent in addition to acetaminophen, the second pharmaceutical agent being selected from the group consisting of antihistamines, antitussives, decongestants, and expectorants.

13. A hard shell gelatin capsule for subsequent oral administration having a hard gelatin shell encapsulating a semi-solid or solid fill, the fill consisting essentially of a pharmaceutically acceptable highly concentrated solution of acetaminophen comprising from about 20% to about 40% by weight acetaminophen, from about 18% to about 65% polyethylene glycol by weight, said polyethylene glycol having an average molecular weight of between about 600 and about 100,000, from about 0% to about 15% propylene glycol by weight, from about 0% to about 15% water by weight, from about 0% to about 15% polyvinylpyrrolidone by weight and from about 0.6% to about 25% of an alkali metal acetate by weight, the alkali metal acetate being present in an amount sufficient to increase the maximum solubility of the acetaminophen in the solution, the alkali metal acetate being selected from the group consisting of sodium acetate and potassium acetate.

14. The capsule according to claim 13 wherein the polyethylene glycol has an average molecular weight of between about 2,000 and 8,000.

15. The capsule according to claim 13 wherein the alkali metal acetate is present in an amount from about 3% to about 20% by weight.

16. The capsule according to claim 13 wherein the fill additionally comprises a second pharmaceutical agent in addition to acetaminophen, the second pharmaceutical agent being selected from the group consisting of antihistamines, antitussives, decongestants, and expectorants.

* * * * *